US00PP22318P2

(12) United States Plant Patent
Meilland

(10) Patent No.: US PP22,318 P2
(45) Date of Patent: Dec. 13, 2011

(54) FLORIBUNDA ROSE PLANT NAMED 'MEITRIPINE'

(50) Latin Name: *Rosa hybrida*
Varietal Denomination: Meitripine

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/801,439

(22) Filed: Jun. 9, 2010

(51) Int. Cl.
*A01H 5/00* (2006.01)

(52) U.S. Cl. ..... Plt./141
(58) Field of Classification Search ..... Plt./141
See application file for complete search history.

*Primary Examiner* — Kent L Bell
(74) *Attorney, Agent, or Firm* — Buchanan Ingersoll & Rooney PC

(57) ABSTRACT

A new and distinct variety of Floribunda rose plant is provided that forms in abundance on a substantially continuous basis attractive very fragrant double blossoms that are lavender in coloration. The buds are pointed and oval in configuration. The vegetation is strong and vigorous and a rounded and bushy growth habit is displayed. The ornamental foliage is dark green with a glossy upper surface and contrasts well with the lavender blossoms. The plant is particularly well suited for providing attractive ornamentation.

1 Drawing Sheet

Botanical/commercial classification: *Rosa hybrida*/Floribunda Rose Plant.

Varietal denomination: cv. Meitripine.

SUMMARY OF THE INVENTION

The new variety of *Rosa hybrida* Floribunda rose plant was created in France by artificial pollination wherein two parents were crossed which previously had been studied in the hope that they would contribute the desired characteristics. The female parent (i.e., the seed parent) was the unreleased product of the cross of the 'Meivildo' variety (U.S. Plant Pat. No. 6,895) and the 'Doris Tysterman' variety (non-patented in the United States). The male parent (i.e., the pollen parent) was the unreleased product of the cross of the 'Korblue' variety (non-patented in the United States) and the 'Delbiop' variety (non-patented in the United States). The 'Delbiop' variety is marketed under the LANCOME trademark. The parentage of the new variety can be summarized as follows:

('Meivildo'×'Doris Tysterman')×('Korblue'×'Delbiop').

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a rounded and bushy growth habit,
(b) forms strong and vigorous vegetation,
(c) abundantly and substantially continuously forms attractive double lavender blossoms that are very fragrant,
(d) displays attractive ornamental glossy dark green foliage, and
(e) is particularly well suited for providing attractive ornamentation.

The new variety well meets the needs of the horticultural industry. It can be grown to advantage as attractive ornamentation in parks, gardens, public areas, and residential settings.

It is particularly well suited for growing in a western United States landscape. The lavender blossoms contrast nicely with the glossy dark green foliage.

The new variety can be readily distinguished from its ancestors. For instance, the 'Meivildo' variety is a Hybrid Tea that forms deep pink blossoms, the 'Doris Tysterman' variety is a Hybrid Tea that forms tangerine and gold blossoms, the 'Korblue' forms blossoms commonly display a lesser number of petals that are lilac mauve in coloration, and the 'Delbiop' variety is a Hybrid Tea that forms blossoms that are deep pink in coloration and are lacking in fragrance.

When compared to the 'Angel Face' variety (non-patented in the United States), the new variety is more vigorous, more floriferous, and commonly displays a more attractive well-balanced rounded and bush growth habit.

The new variety has been found to undergo asexual propagation in France and at Wasco, Calif., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meitripine'.

BRIEF DESCRIPTION OF THE PHOTOGRAPH

The accompanying photograph shows, as nearly true as it is reasonably possible to make the same in a color illustration of this character, typical blossoms of the new variety. The pointed oval-shaped buds also are illustrated. The depicted plant was approximately two years of age and was being grown outdoors during October 2008 at Wasco, Calif., U.S.A.

DETAILED DESCRIPTION

The chart used in the identification of the colors is that of The Royal Horticultural Society (R.H.S. Colour Chart)

except where ordinary color terms are utilized. Such common color terms are to be accorded their customary dictionary significance. The description is based upon the observation of plants of the new variety at an age of approximately two years during the month of May while being grown in containers near West Grove, Pa., U.S.A.

Class: Floribunda.

Plant:

*Growth habit.*—Vigorous, rounded and bushy.

*Blooming habit.*—Abundant and substantially continuous.

*Height.*—Commonly approximately 3 feet at maturity.

*Width.*—Commonly approximately 3 feet at maturity.

Branches:

*color.*—Young stems: commonly near Yellow-Green Group 144B. Adult wood: commonly near Yellow-Green Group 146B. Length: commonly approximately 20 cm. Diameter: commonly approximately 4 mm. Internode length: commonly approximately 2.5 to 3 cm.

*Thorns.*—Size: commonly approximately 3 mm in length on average when immature, and approximately 6 mm in length on average when mature. Color: commonly near Greyed-Yellow Group 161B when immature, and near Brown Group 200D when mature. Shape: erect with a narrow oval base. Quantity: commonly approximately 5 to 8 per internode length.

Leaves:

*Overall appearance.*—Attractive dark green.

*Leaflets.*—Shape: generally ovate with a rounded base and an acuminate tip. number: 3, 5, and 7 per leaf. Size: the terminal leaflets commonly are approximately 6.5 cm in length on average, and approximately 4.5 cm in width at the widest point on average, and the remaining leaflets commonly are approximately 3 cm in length on average and approximately 1.5 cm in width at the widest point on average. Serration: small and single. Texture: smooth and glossy on the upper surface, and smooth with a coarse midrib on the under surface. Color (young foliage): on the upper surface commonly near Greyed-Red Group 179A with tones of near Yellow-Green Group 152C towards the midrib, and on the under surface commonly near Greyed-Red Group 179A with tones of Yellow-Green Group 152C towards the midrib. Color (adult foliage): on the upper surface near Green Group 137B, and on the under surface near Green Group 138B.

*Stipules.*—Shape: commonly turn outward at an angle greater than 45° and often recurve toward the stem. Length: commonly approximately 2 cm. Width: commonly approximately 6 mm. Apex: acute. Margin: entire. Color: near Yellow-Green Group 144A.

*Petiole.*—Length: Commonly approximately 2 cm. Diameter: commonly approximately 2 mm. Color: near Yellow-Green Group 144A.

*Rachis.*—Length: commonly approximately 4.5 cm. Diameter: commonly approximately 1 mm. Color: near Green Group 138A.

Inflorescence:

*Number of flowers.*—Typically in clusters of three to five flowers and commonly with up to 20 or more open blossoms being present on an individual plant at one time.

*Peduncle.*—Commonly approximately 6 to 10 cm in length on average, commonly approximately 3 mm in diameter on average, and near Yellow-Green Group 144B in coloration.

*Sepals.*—Number: five. Shape: generally lanceolate. Apex: acute. Base: truncate. Margin: mostly entire and slightly incised towards the apex. Size: commonly approximately 3 cm in length on average, and approximately 5 mm in width on average at the widest point. Texture: smooth on both surfaces. Color: on the upper surface commonly near Yellow-Green Group 144C, and on the under surface commonly near Yellow-Green Group 144A.

*Buds.*—Shape: ovoid and pointed. Length: approximately 3 cm on average. Width: approximately 1.3 cm on average at the widest point. Color as calyx breaks: commonly near Red-Purple Group 71C.

*Flower.*—Form: double and ruffled. Diameter: approximately 10 cm on average. Color (when opening begins): upper surface: commonly between Purple Group 75B and Purple Group 75C. under surface: commonly between Purple Group 75B and Purple Group 75C. Color (at end of blooming): upper surface: commonly between Purple Group 76B and Violet Group 84C. under surface: commonly between Purple Group 76B and Violet Group 84C. Fragrance: very strong and similar to Citrus and Verbena. Lasting quality: the blossoms commonly last approximately 7 days on average on the plant depending upon environmental conditions, and approximately 5 to 6 days on average when cut and placed in a vase. Petal length: commonly approximately 3.5 cm. Petal width: commonly approximately 3 cm. Petal apex: obtuse. Petal base: rounded. Petal margin: entire. Petal texture: smooth on both surfaces. Petal number: approximately 25 to 27 on average under normal growing conditions. Petal arrangement: imbricated. Petal drop: good with the petals commonly detaching cleanly before drying. Stamen number: approximately 60 to 70 on average. Anthers: coloration commonly varies from Yellow-Orange Group 20A to Greyed-Orange Group 175D. Filaments: commonly approximately 5 to 8 mm in length on average, and near Yellow Group 11D in coloration. Pollen: commonly formed in a sparse quantity, and near Yellow-Orange Group 20B in coloration. Pistils: separate and free, and approximately 50 in number on average. Styles: commonly approximately 3 mm in length on average, and near Greyed-Yellow Group 161D in coloration. Stigmas: commonly approximately 1 mm in diameter, and near Greyed-Yellow Group 161D in coloration. Receptacle: generally ovoid in shape, approximately 5 mm in length on average, approximately 4 mm in diameter, generally smooth in texture, near Yellow-Green Group 144A in coloration, and achenes stand on the bottom and wall. Hips: none observed.

Development:

*Vegetation.*—Vigorous and strong.

*Blooming.*—Abundant and substantially continuous.

*Resistance to diseases.*—During observations to date, average resistance with respect to Black Spot, Mildew, and Rust.

I claim:

1. A new and distinct Floribunda rose plant characterized by the following characteristics:

(a) exhibits a rounded and bushy growth habit, (b) forms strong and vigorous vegetation, (c) abundantly and substantially continuously forms attractive double lavender blossoms that are very fragrant, (d) displays attractive ornamental glossy dark green foliage, and (e) is particularly well suited for providing attractive ornamentation;

substantially as shown and described.

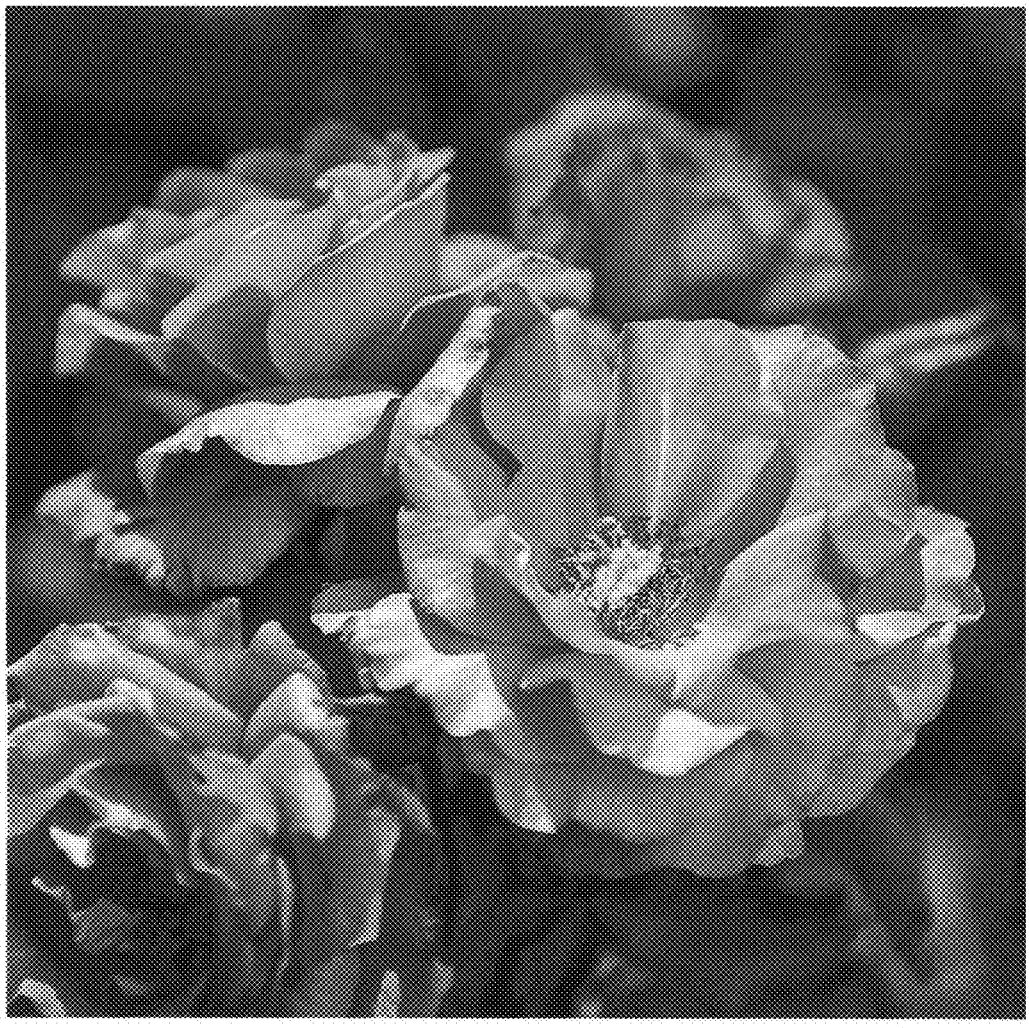

* * * * *